(12) United States Patent
Greenwood (10) Patent No.: US 7,966,882 B2
(45) Date of Patent: Jun. 28, 2011

(54) SELF-CALIBRATING METHOD FOR MEASURING THE DENSITY AND VELOCITY OF SOUND FROM TWO REFLECTIONS OF ULTRASOUND AT A SOLID-LIQUID INTERFACE

(75) Inventor: Margaret Stautberg Greenwood, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 613 days.

(21) Appl. No.: 12/108,161

(22) Filed: Apr. 23, 2008

(65) Prior Publication Data
US 2009/0266165 A1 Oct. 29, 2009

(51) Int. Cl.
*G01N 9/24* (2006.01)
(52) U.S. Cl. ............ 73/597; 73/30.01; 73/32 A; 73/602; 73/61.79
(58) Field of Classification Search .............. 73/30.01, 73/30.04, 32 A, 597, 598, 599, 600, 602, 73/54.01, 54.41, 61.49, 61.79
See application file for complete search history.

(56) References Cited

U.S. PATENT DOCUMENTS

| | | | |
|---|---|---|---|
| 5,365,778 A | 11/1994 | Sheen et al. | |
| 5,708,191 A | 1/1998 | Greenwood et al. | |
| 5,886,250 A | 3/1999 | Greenwood et al. | |
| 6,082,181 A | 7/2000 | Greenwood | |
| 6,763,698 B2 | 7/2004 | Greenwood | |
| 6,877,375 B2 | 4/2005 | Greenwood | |
| 7,140,239 B2 | 11/2006 | Greenwood et al. | |
| 2005/0215902 A1 | 9/2005 | Greenwood | |

FOREIGN PATENT DOCUMENTS

WO  WO2007/058391 A1  5/2007

OTHER PUBLICATIONS

International Search Report/Written Opinion.
Greenwood, Margaret Stautbert, et al., Measurement of Viscosity and Shear Wave Velocity of a Liquid or Slurry for On-Line Process Control, Ultrasonics 39 (2002) 623-630.

*Primary Examiner* — Daniel S Larkin
(74) *Attorney, Agent, or Firm* — Derek H. Maughan (57) ABSTRACT

A method for determining a velocity and density of a fluid without requiring the transmission of ultrasound through the fluid, and a system for performing such a method. The method involves the steps of delivering, receiving and analyzing ultrasound pulses sent from a longitudinal and a shear wave transducers to a member that is in contact with a fluid. The ultrasound pulses reflecting between surfaces provide a first ultrasound pulse echo series, that is transmitted, received and processed. The shear wave ultrasound pulses are also delivered through a shear wave transducer at a predesignated angle relative to the interface of the member and the fluid and the results of this are received to obtain a second ultrasound pulse echo series. Reflection coefficients for the first and second ultrasound pulse echo series are then calculated and the density of the fluid and the velocity of sound in the fluids are extracted.

12 Claims, 6 Drawing Sheets

SELF-CALIBRATING METHOD FOR MEASURING THE DENSITY AND VELOCITY OF SOUND FROM TWO REFLECTIONS OF ULTRASOUND AT A SOLID-LIQUID INTERFACE

BACKGROUND

1. Field of the Invention

The present invention relates to fluid analysis and more particularly, but not exclusively, to the determination of fluid properties at a solid-liquid interface without the necessity of timing the passage of ultrasound through the liquid.

2. Background of the Invention

Fluids are encountered in a wide variety of industrial applications and there is a continual need to determine properties of those fluids. A variety of methods exist, including those set forth by the present inventor in U.S. Pat. No. 6,763,698 and U.S. Pat. No. 6,877,375, the contents of which are herein incorporated by reference. The present invention provides an improved method for determining characteristics of a liquid or slurry without requiring the passage of ultrasound through this media. The present invention also allows for increased accuracy in making determinations related to the materials being tested, as well as avoids problems associated with other methods such as the impact of bubbles, attenuative fluids, or large sample volumes upon proper determinations.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

BRIEF DESCRIPTION OF THE VIEWS OF THE DRAWING

FIG. 2b is a detailed view of an alternate embodiment of the system shown in FIG. 2a.

DETAILED DESCRIPTION

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein, are contemplated as would normally occur to one skilled in the art to which the invention relates.

Figure 1:
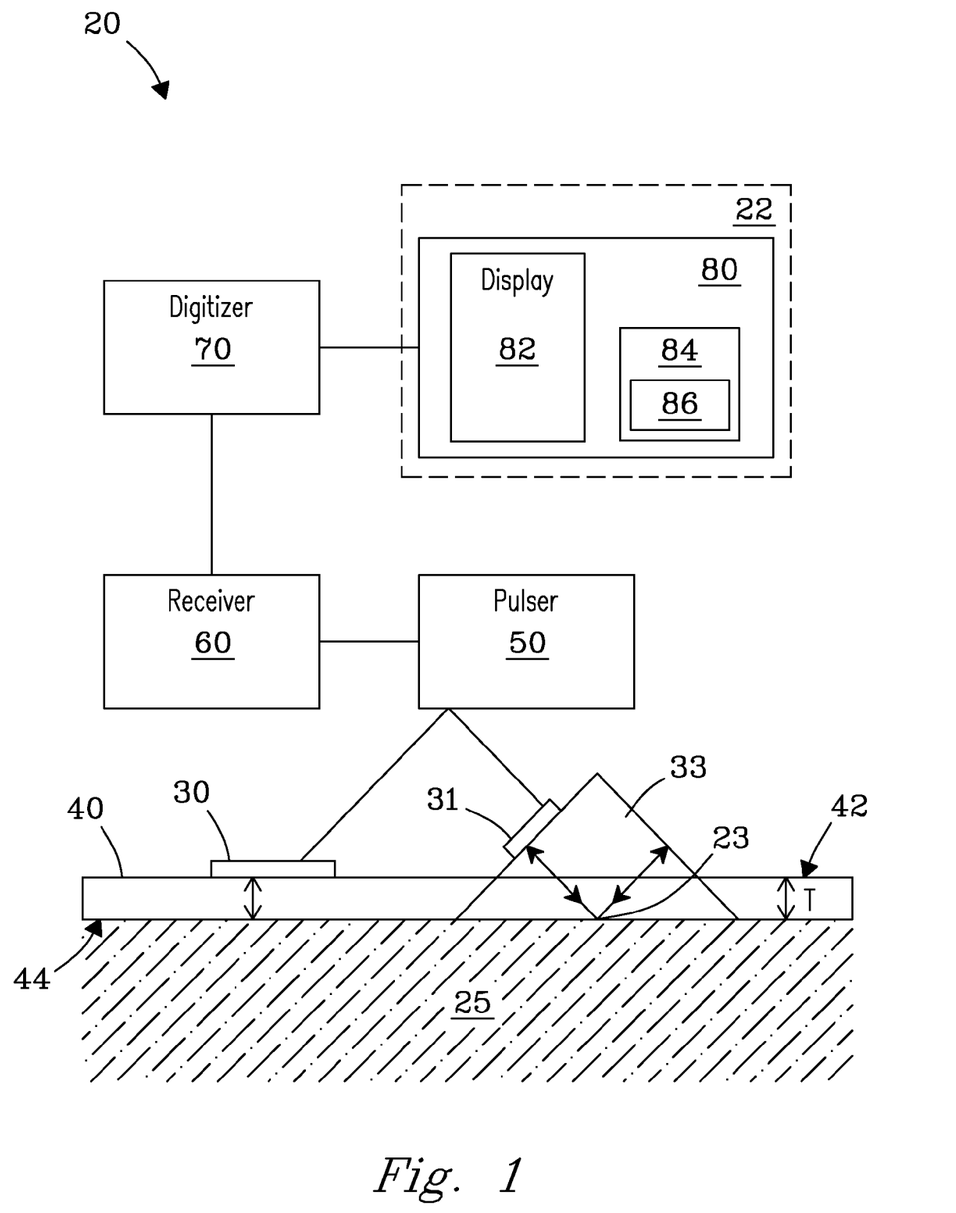
FIG. 1 is a diagrammatic view of system for determining fluid properties.

Turning now to FIG. 1, a system 20 for analyzing a property of fluid 25 is depicted. Fluid 25 can be a gas, liquid, slurry, suspension, paste, emulsion and the like. In preferred forms, fluid 25 is substantially non gaseous and/or includes at least one liquid. In this form, fluid 25 might be, for example, a liquid, slurry, or suspension. Ultrasonic transducer 30 is acoustically coupled to a first surface 42 of a member 40 comprised of a solid material. In one example, transducer 30 is in direct contact with member 40. In other examples, one or more couplants might be used between transducer 30 and member 40, or they may be coupled as would otherwise occur to those skilled in the art. An opposed second surface 44 of member 40 is in contact with the fluid 25. A pulser 50 is electrically coupled to transducer 30 and is operable to deliver input stimulus signal to transducer 30 to cause transducer 30 to emit acoustic energy through solid member 40 and towards fluid 25. Transducer 30 is also operable to produce output signals in response to acoustic energy transmitted from member 40.

A shear wave inducing transducer 31 is also mounted to the member 40 in a manner so that transmissions propogated by the shear wave inducing transducer 31 are reflected off of the interface 23 of the member 40 and the surface of the fluid 25 being analyzed. In the preferred embodiment this shear wave inducing transducer emits ultrasound at a generally 45 degree angle to the surface/fluid interface 23 through an angle block 33 which may be attached as a portion of the member 40 itself. The shear wave transducer 31 produces transverse waves that are perpendicular to the direction of motion of the wave. In addition, shear wave transducer 31 is oriented on member 40 so that shear-vertical waves SV are produced. For purposes of understanding the directions of these waves in relation to the other portions of the device, in a shear wave transducer, the vibrations are in the plane of the paper and shear horizontal waves SH producing vibrations that are perpendicular to the plane of the paper. The reflection of SV and SH waves at a solid-liquid interface 23 are extremely different.

Figure 2A:
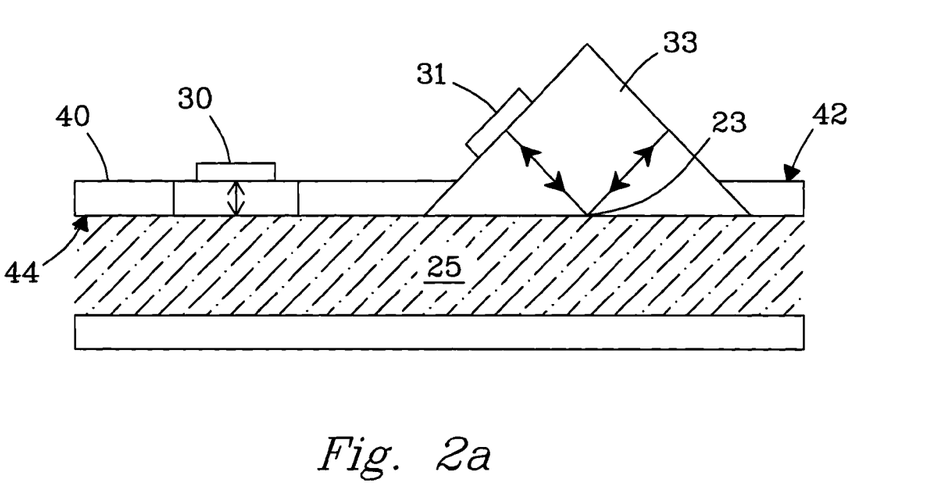
FIG. 2a is a detailed view of the portion of the system shown in FIG. 1.
Figure 2B:
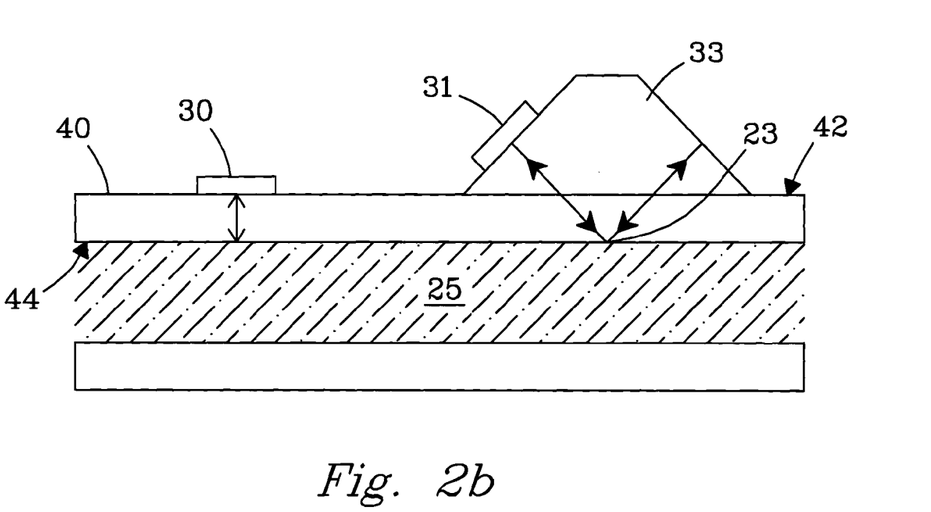

In the embodiment shown in FIG. 2a, this angle block 33 which is made of a material such as quartz and is positioned within a window whereby the angled transmission from the angled transducer 31 to the interface 23 does not pass through any other materials that are not a part of the angle block 33. In an alternative embodiment shown in FIG. 2(b) the shear wave transducer 31 and the angle block 33 are connected to the outer portion of the conduit member 40. In such an embodiment the angle block 33 is made from a material such as stainless steel or other similar types of material. This angle block is generally configured so that the shear wave transducer 31 is positioned at a general angle of 45°. This angle is generally preferred because a reflected longitudinal wave cannot generally occur at this angle. In addition to transmitting at a 45° angle this angle block 33 also serves to reflect transmitted shear waves back towards the interface 23, and in turn back towards the shear wave emitting transducer 31. These reflected waves are also received by the shear wave inducing transducer 31 which then transmits a quantity of information related to this wave back to the processing apparatus 22.

In one embodiment, the processing apparatus 22 including receiver 60, digitizer 70, and computer 80, is coupled to pulser 50 and to transducers 30, 31. Processing apparatus 22 controls delivery of output signals to each of the two transducers 30, 31 and receives the input signals from the transducers 30, 31 and, as described more fully below, performs calculations to determine properties of fluid 25 based upon the receipt of transducer output signals.

In operation, pulser 50 generates and delivers a short duration stimulus to transducers 30, 31. Transducer 30 responds to the stimulus by emitting a longitudinal. wave pulse of ultrasound into member 40. This ultrasonic pulse reflects between surfaces 44 and 42 producing a series of pulse echoes at t ansducer 30. This resulting echo series will be of successively diminishing echo amplitude because each successive echo will have reflected from the solid fluid interface at surface 44 one time more than the previous echo. in a similar fashion shear wave transducer 31 responds to the stimulus by emitting a shear wave pulse of ultrasound to the interface 23 between member 40 and the fluid 25. This ultrasonic pulse reflects off of the interface 23 and in the preferred embodiment into the angle block 31. The air on the opposing side of the angle block 31 then reflects preferably 100 percent of this ultrasonic pulse back toward the interface surface 23 and then back to the shear wave transducer 31 producing a series of pulse echoes at shear wave transducer 31.

Transducers 30, 31 respond to the echoes by producing an output signal proportional to the echo amplitude that is amplified by receiver 60, digitized by digitizer 70 and passed to computer 80. Computer 80 includes programming instructions encoded on fixed and/or removable memory devices 84, 86, respectively, to gather the select a peak echo amplitude for the series echoes and to determine the average decay rate of the peak echo amplitudes with increasing echo number in the echo series. Alternatively, computer 80 can be at least partially hard wired with dedicated memory devices and configured to execute logic according to the present invention. Computer 80 is operatively coupled to display 82 to output selected information about fluid 25 integrated with transducers 30, 31.

A shear wave transducer is used for transducer 31 rather than a longitudinal one because when a longitudinal wave strikes a solid-liquid interface at an angle (no matter the size of the angle), the following will always be produced: (1) a reflected longitudinal wave at the same angle as the incident one, (2) a mode-converted shear wave at about half the angle of the incident longitudinal (depending upon Snell's Law) and (3) a transmitted longitudinal wave in the liquid. Thus, if the reflected longitudinal waves are observed, there would be only a few reflections (particularly for stainless steel) because energy has been used to create the mode-converted shear waves.

When a shear wave transducer (SV mode of operation) is used at small incident angles with the vertical, a mode-converted reflected longitudinal wave is produced. That is, all three types of waves are produced as has just been discussed in the preceding paragraph. However, when the incident angle is 45°, a reflected shear wave is produced, but a reflected mode-converted longitudinal wave simply cannot be produced. The reason is that the reflected longitudinal wave always has a greater angle than the reflected shear wave, but at some incident angle (slightly less than 45°) the mode-converted longitudinal wave becomes 90°. Since 90° is the limit for the mode-converted reflected longitudinal wave, this wave is simply not produced at 45°. For a shear wave incident upon a solid-liquid interface at a 45°, two types of waves are produced: (1) reflected shear wave and (2) a transmitted longitudinal wave in the liquid. Therefore, when the reflected shear wave is observed, energy is available for many reflections. In summary, more reflections are observed using a SV shear wave transducer at an incident angle of 45° than would be obtained using a longitudinal transducer.

The transducers 30, 31 can be applied to any solid unit, but there are two materials that have special significance for process control: (1) stainless steel and (2) fused quartz. Fused quartz is often used as windows in a pipeline and the pipeline is often constructed of stainless steel. Fused quartz has a very low attenuation of ultrasound and so is a very good choice for the material. Stainless steel may be preferred in some cases, but it can be quite attenuative. For this reason, the experiments were carried out to show that this method can be applicable even for stainless steel.

Preferably a number of echo amplitudes, for example [5] five or more, spanning a range of echo numbers are used in computing the decay rate both the longitudinal wave reflections emanating and being reflected through transducer 30, as well as the shear wave reflections being sent from sent from shear wave transducer 31. This feature referred to at times as "self-calibration" preferably occurs with the information received from each of the two transducers. Information from the longitudinal transducer 30 yields the reflection coefficient for ultrasound perpendicular to the solid-liquid interface, while that from the shear wave transducer 31 yields the reflection coefficient for ultrasound incident at 45°. In one preferred form, each reflection coefficient depends upon the density of the liquid or slurry that is being measured and the velocity of the sound in the liquid. By then solving these two equations for each of these two unknowns, the density and velocity of the sound in the liquid can be determined.

In one embodiment the computer 80 is programmed to first compute the fast Fourier transform (FFT) of the digitized signals, converting them from the time domain to the frequency domain and then determine the peak amplitude at a selected frequency, where the frequency is selected to be, for example, the center frequency of transducer 30 and transducer 31.

The objective is to compare the experimental measurement of each reflection coefficient with a theoretical calculation and to extract the density of the material and the velocity of sound. The experimental measurement of the perpendicular coefficient and the coefficient at a 45° are both measured by looking at the multiple echo pattern. However, each set of multiple reflections has a different decay rate and hence, a different value for the reflection coefficient. The following description applies to both types of reflections.

The FFT amplitude at a given frequency is proportional to $RC^N$, where RC is the reflection coefficient and N is the echo number.

$$V \alpha RC^N \tag{1}$$

For example, if the RC is 0.8, then the amplitude of the $5^{th}$ echo is equal to 0.32768 C and that of the first echo, equal to 0.8 C, where C is a constant of proportionality. Thus, the amplitude of the $5^{th}$ echo is about 41% of that for the first echo.

This proportionality can be written for a liquid and for water. For the same experimental setup, the (unknown) constant of proportionality is the same for both. Thus, the constant of proportionality drops out when the two equations are divided.

$$V\text{liq}(N)/V\text{wtr}(N) = RC\text{liq}^N/RC\text{wtr}^N \tag{2}$$

Taking the natural logarithm of both sides yields the following:

$$\text{Ln}(V\text{liq}(N)/V\text{wtr}(N)) = N \ln(RC\text{liq}/RC\text{wtr}) \tag{3}$$

Vliq is identified as the EFT amplitude for a liquid and similarly defined for Vwtr, When the left-hand quantity is plotted on the vertical axis (y) of a graph and the echo number N, on the horizontal axis (x), then the result is a straight line, y=mx+b in the standard form. The quantity m is the slope and b is the intercept on the y-axis. The slope of the straight line is given by $$\text{Slope} = \ln(RCliq/RCwtr) \quad (4)$$

Eq. (4) can be rewritten as follows:

$$RCliq = RCwtr\, e^{Slope} \quad (5)$$

In summary, the reflection coefficient for ultrasound striking a solid-liquid interface can be obtained by plotting the natural logarithm of the quantity (Vliq/Vwtr) versus the echo number and finding the slope of the line. The reflection coefficient RCliq is then determined from Eq. (5). The reflection coefficient RCwtr is determined from well-known formulations for the reflection coefficient, such as Krautkramer and Krautkramer (1990).

The above method uses the FFT amplitude at one frequency—one point on the amplitude-versus-frequency curve—but greater accuracy can be achieved by using several points as the following demonstrates. In this preferred application of the present invention the reflection coefficient does not depend upon frequency. While the peak of the FFT amplitude curve at a frequency f1 has usually been chosen, it is by no means unique. The quantity V(f2, N) is defined as the FFT amplitude at frequency f2 for echo N. Thus, it is another point of the EFT amplitude curve. Writing Eq. (3) for three frequencies f1, f2, and f3 yields the following:

$$\text{Ln}(Vliq(f1,N)/Vwtr(f1,N)) = N \ln(RCliq/RCwtr) \quad (6)$$

$$\text{Ln}(Vliq(f2,N)/Vwtr(f2,N)) = N \ln(RCliq/RCwtr) \quad (7)$$

$$\text{Ln}(Vliq(f3,N)/Vwtr(f3,N)) = N \ln(RCliq/RCwtr) \quad (8)$$

Adding the three equations together and realizing that the summation of logarithms is the same as products yields:

Ln [Vliq(f1,N)Vliq(f2,N)Vliq(f3,N)/Vwtr(f1,N)Vwtr(f2,N)Vwtr(f3,N)]=3 $N \ln(RCliq/RCwtr)$ (9) This can be rewritten as:

Ln [$Vliq(f1,N)Vliq(f2,N)Vliq(f3,N)/Vwtr(f1,N)Vwtr(f2,N)Vwtr(f3,N)$]$^{1/3}$=$N \ln(Rliq/Rwtr)$ (10)

In this case, the quantity on the left side of Eq. (10) is plotted versus the echo number N, where the slope on this plot is determined. As before, the reflection coefficient is obtained using Eq. (4) and Eq. (5).

Eq.(5) shows that in order to determine the reflection coefficient for the liquid the theoretical formulation is required in order to determine the reflection coefficient for water for the perpendicular incidence and for incidence at 45°

A, Perpendicular Incidence

The formulation for the reflection coefficient for ultrasound traveling in a solid and striking the solid-liquid interface perpendicularly is given by:

$$RC = (Zliquid - Zsolid)/(Zliquid + Zsolid) \quad (11)$$

Z is the acoustic impedance defined as the density multiplied by the velocity of sound. For a calibration liquid, such as water and the known solid, the acoustic impedance of both the liquid and solid are known and so the RCwater can be determined.

From Eq. (5), the RCliquid can be determined from the reflection coefficient for water and the slope of the line on a plot, as has been discussed.

From the fluid specific reflection coefficient (RCfluid), computer 80 calculates the acoustic impedance of the fluid (Zfluid) according to Eq. (12).

$$Zliquid = Zsolid(1 - RCliquid)/(1 + RCliquid) \quad (12)$$

where Zsolid is the acoustic impedance of the solid member 40. Eq. (12) was obtained by solving Eq. (11) for Zliquid.

The acoustic impedance of the fluid (Zliquid is defined as follows:

$$Zliquid = (\text{density of the liquid}) \quad (13)$$
$$(\text{velocity of sound in the liquid}) =$$
$$= \rho c$$

Where $\rho$ is the density of the liquid and c is the speed of the sound in the liquid. A value has been obtained for the acoustic impedance of the liquid, but there are two unknowns: $\rho$ and c. A second equation is obtained from the incidence at an angle of 45°, which is discussed next.

B. Incidence at 45° angle at solid-liquid interface

Eq. 5). shows that in order to determine the reflection coefficient for ultrasound striking the solid-liquid interface at 45°, a theoretical calculation of the reflection coefficient for water (or the calibration liquid) is needed and the "Slope" obtained from experimental measurements of multiple reflections, as discussed above. This procedure yields the experimental value of the reflection coefficient at 45°.

The objective of the measurements is to obtain values for the reflection coefficient at 90° ($RC_{90}$) and at 45° ($RC_{45}$). Since the theoretical equations include the density of the liquid and the velocity of sound in the liquid (which are unknown), as well as known properties of the solid and calibration liquid, the two unknown quantities can be determined. The following is a formulation for the reflection coefficient for SV shear waves striking a solid-liquid interface at an angle.

Figure 3:
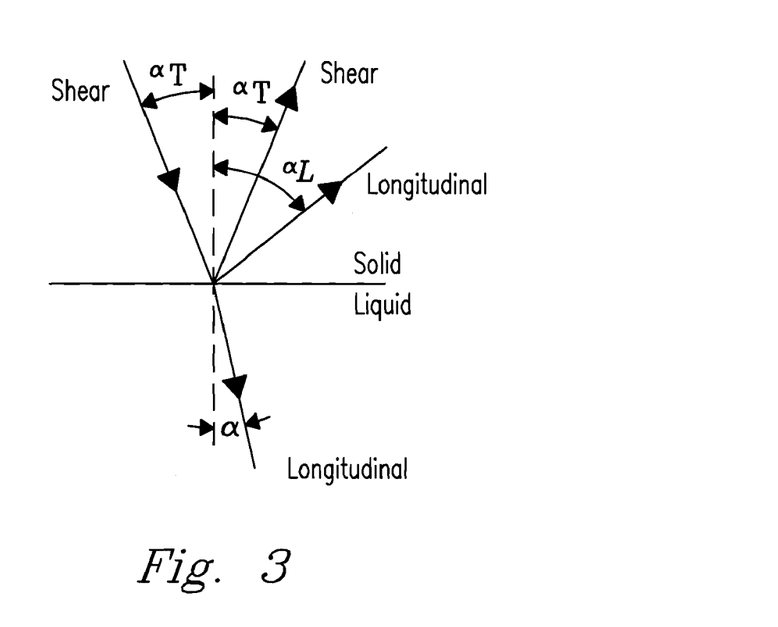
FIG. 3 is a view of an incident wave against a surface.

Referring now to FIG. 3, FIG. 3 shows a shear wave striking a surface at an angle $\alpha_T$ and a reflected shear wave at angle $\alpha_T$. For some incident angles $\alpha_T$, a longitudinal wave is also produced in the solid at angle $\alpha_L$ and the restrictions will be discussed shortly. A longitudinal transmitted wave is also produced in the liquid at angle $\alpha$. The longitudinal velocity in the solid is denoted by $c_L$ and the shear wave velocity, by $c_T$. The velocity of sound in the liquid is given by c. The density of the solid is given by $\rho_f$ and the density of the liquid by $\rho$.

As the angle $\alpha_T$ increases, the angle $\alpha_L$ also increases. The angle $\alpha_L$ cannot increase, obviously, beyond 90°. Thus, for some angle $\alpha_T$, a longitudinal wave is simply not possible and does not exist. For a steel-water interface, this critical angle is about 33°. Beyond 33° the reflected longitudinal waves are not present. This is very advantageous because all of the reflected energy will be concentrated in the reflected shear wave. Calculations of the reflection coefficients for an incident angle $\alpha_T$ less than 33°, can be calculated according to the known formulas such as the one described by Krautkramer and Krautkramer (1990). However, for larger angles, the formulae are not provided but a method of derivation for obtaining such a value is described. Because the incident angle in these experiments is 45°, a derivation was carried out and the resulting reflection coefficient Rtt (using the notation of Krautkramer and Krautkramer) is given by:

$$Rtt = \{[(N1-N3)^2 + N2^2]/[(N1+N3)^2 + N2^2]\}^{0.5} \quad (14)$$

The parameter Con is defined as follows:

$$Con = (c_L/c_T)\sin \alpha_T \quad (15)$$

N1, N2, and N3 are defined as follows:

$$N1 = (c_T/c_L)^2 [2Con(Con^2-1)^{0.5}] \sin 2\alpha_T \quad (16)$$

$$N2 = \cos^2 2\alpha_T \quad (17)$$

$$N3 = (\rho c/\rho_f c_L)(Con^2 - 1)^{0.5}/\cos\alpha \quad (18)$$

For an incident angle of 45°, the term for N2 is equal to 0 and the reflection coefficient reduces to $$Rtt = (N1 - N3)/(N1 + N3) \quad (19)$$

One objective is to show that the density and velocity of sound can be obtained from $RC_{90}$ and $RC_{45}$. The above equations show that this is possible. In Eq. (16) for N1, all of the quantities are known and so N1 can be evaluated numerically. in Eq (18) for N3, there are two unknown terms: $\rho$ c and cos $\alpha$, where $\alpha$ is the angle of the transmitted beam in the liquid. Solving Eq (19) for N3 and using the syn bol RC45 for Rtt, we find the following:

$$N3 = N1(1 - RC45)/(1 + RC45) \quad (20)$$

Therefore, N3 can be evaluated since values have been obtained for both N1 and RC45.

In Eq (18) for N3, there are two unknown terms: $\rho$ c and cos $\alpha$, where $\alpha$ is the angle of the transmitted beam in the liquid. However, the acoustic impedance of the liquid $\rho$ c is known from Eq (13) Thus, Eq. (18) can be solved for cos $\alpha$ and, of course, the angle $\alpha$ can also be determined.

The velocity of sound can be determined from Snell's law of refraction, as follows:

$$\sin\alpha_T/\sin\alpha = c_T/c \quad (21)$$

Since the angle a has been determined, the only unknown in Eq. (21) is the velocity of sound in the liquid, c. Thus, the velocity of sound can be determined. The density can be determined from the value of the acoustic impedance of the liquid, Zliq.

$$\text{Density of liquid } \rho = Zliq/c \quad (22)$$

The use of the perpendicular measurement of multiple reflections and the self-calibrating feature of these measurements has been documented in U.S. Pat. No. 6,763,698, in which an accurate value of the acoustic impedance of the liquid is obtained. in this technique, the velocity of sound is obtained by measuring the passage of ultrasound through the liquid or slurry. The present invention omits the measurement through the liquid or slurry and instead utilizes the measurement of the SV shear reflection coefficient for incidence at an angle to a solid-liquid interface. The experimental data focuses on the data obtained for incidence at a 45° angle at a solid-liquid interface. The material for the 45° triangular wedge was chosen to be stainless steel, which leads to a more difficult measurement than using fused quartz. Fused quartz results in many echoes.

Figure 4:
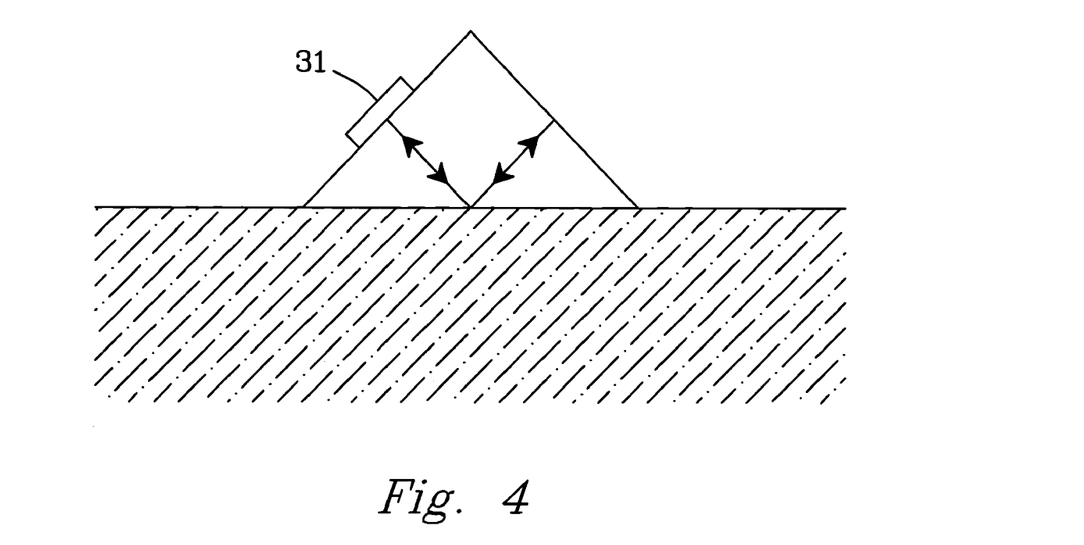
FIG. 4 is a view of a portion of the block of the present invention.

The measurements were performed using a stainless steel (SS304) triangular wedge as shown in FIG. 4. The base of the triangular wedge was immersed in various concentrations of sugar water, for which the density and velocity of sound were measured directly utilizing traditional methods, and then again utilizing the presently described methods. The objective was to show that the experimental measurement of the reflection coefficient is in agreement with the calculations of the reflection coefficient for an incidence of 45°, using known values for the density and velocity of sound in sugar water solutions.

Figure 5:
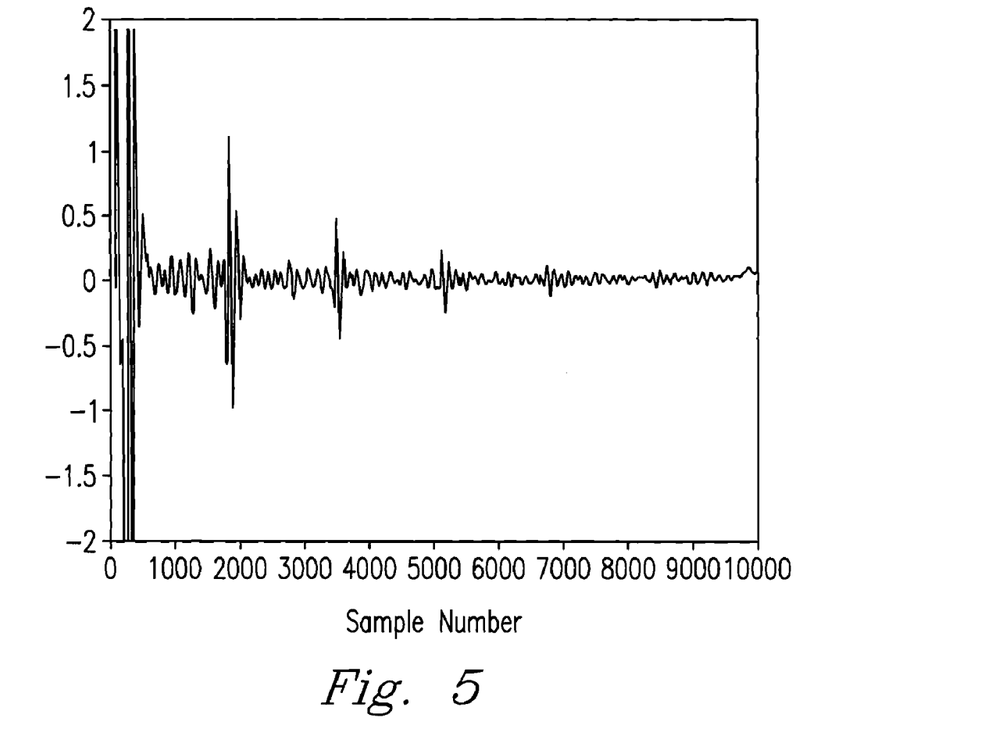
FIG. 5 is a view of multiple echoes.

FIG. 4 the base of the triangle is 1.5 inches and the angles at the base are 45°. A commercial shear wave transducer having a diameter of 0.5 inches and a frequency of 1 MHz was coupled to the unit using shear-wave coupling gel. The shear wave transducer was mounted so as to produce vibrations that create shear vertical waves (ST). A pulse of ultrasound is reflected twice at the solid-liquid interface during each roundtrip. As many as five echoes can e observed by the transducer, as shown in FIG. 5. The advantage of using a 45° angle is that no reflected longitudinal wave in steel can be produced (as discussed previously), while at a smaller angle—say, 20°—a reflected longitudinal wave is produced. Thus, when the incident shear wave strikes the steel-liquid interface only two waves result: 1) the reflected shear wave and 2) the longitudinal wave transmitted into the liquid. As a result, the reflected shear wave has sufficient energy to produce echoes.

Figure 6:
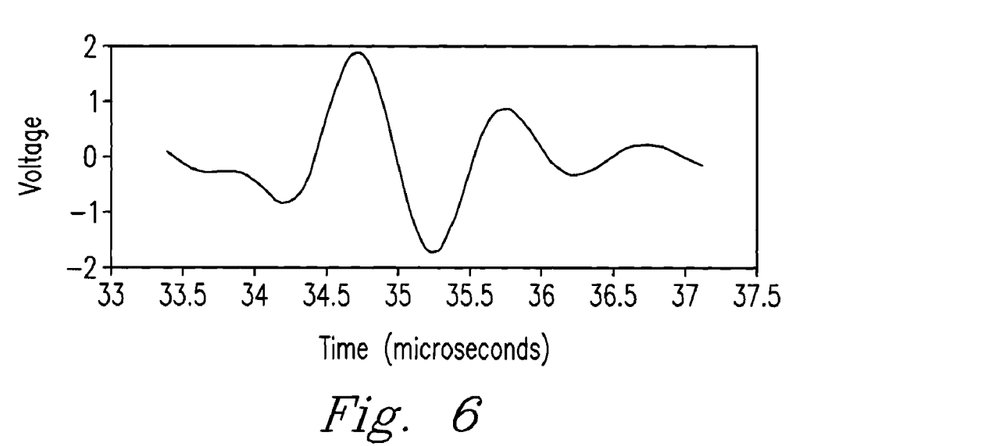
FIG. 6 is a graph of a single echo.
Figure 7:
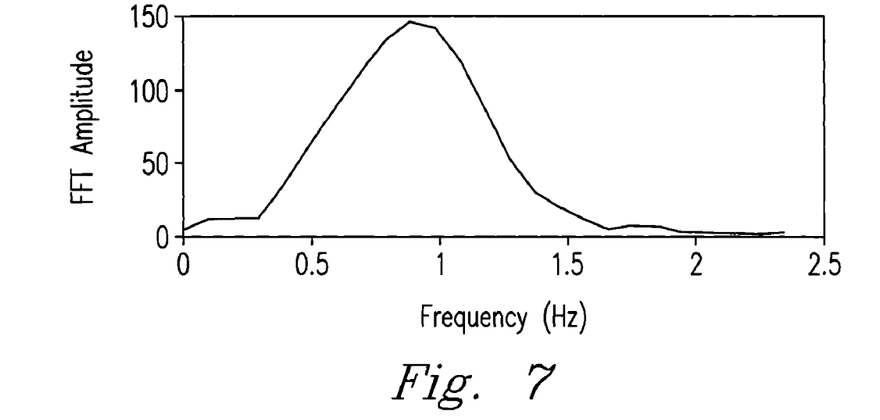
FIG. 7 is a graph of the FFT values for the signal in FIG. 6.

An expanded view of one echo is shown in FIG. 6 and the fast Fourier transform of that signal is shown in FIG. 7. The usual treatment is to take the maximum FFT amplitude for a liquid (or slurry) and compare it with the maximum FFT amplitude for water. The original derivation has been extended to include the amplitude at several frequencies, as this has been discussed and the derivation carried out in Eq.(6) through Eq. (10).

Figure 8:
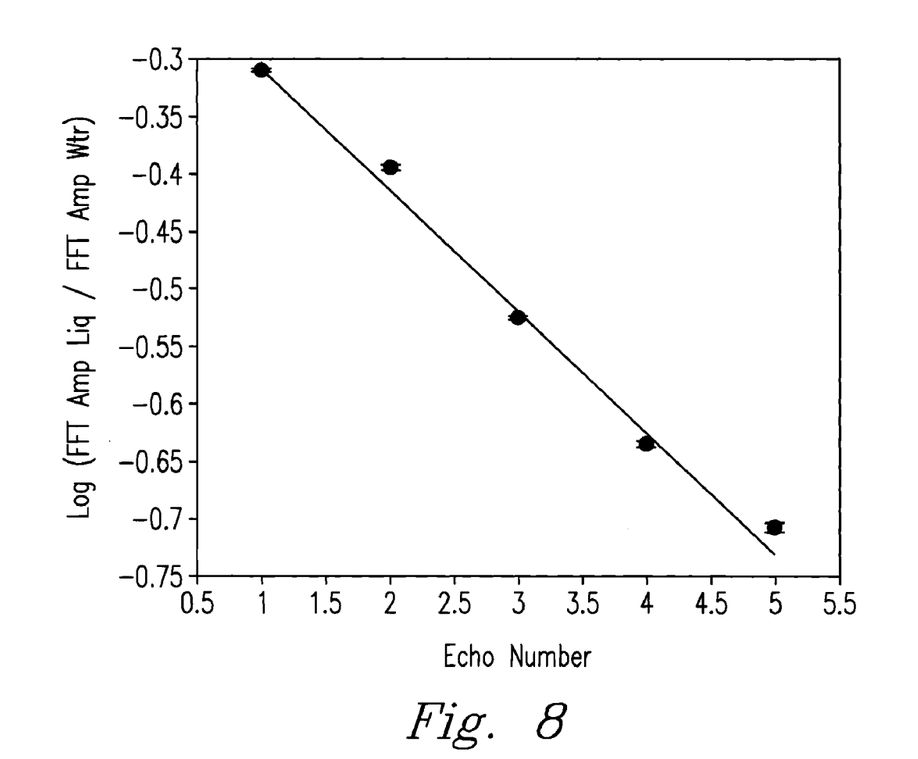
FIG. 8 is a graph relating the natural logarithm of FFT amplitude of each echo divided by that for water to the echo number.

FIG. 8 shows the data obtained for the five echoes for 50% sugar water, using the extended method to obtain the FFT amplitude, as described in Eq. (10). For the sake of simplicity, this is referred to as the PFT amplitude, A similar calculation was obtained for the FFT amplitude for water for five echoes. For each echo, the HT amplitude for a liquid was divided by that for water and the natural logarithm of that quantity was obtained. In FIG. 8 the ordinate is the following: Log (FFT amplitude for liquid for echo N/FFT amplitude for water for echo N), while the abscissa is the echo number N. As described earlier, the reflection coefficient is related to the slope of the line. Similar calculations and graphs were obtained for each liquid.

Because two reflections occur in each round trip, Eq. (5). is modified by including, a factor of 2.

$$RCliq/RCwtr = e^{slope/2} \quad (23)$$

The experimental value of RClig/RCwater was determined using Eq. 23 by finding the slope of the line, similar to that in FIG. 8 for 50% sugar water. The experimental values of the ratio RCliq/RCwtr for six sugar water solutions are plotted versus the sugar water concentration in FIG. FIG. 9 using a diamond shape and the theoretical values of the ratio RCliq/RCwir by squares.

Figure 9:
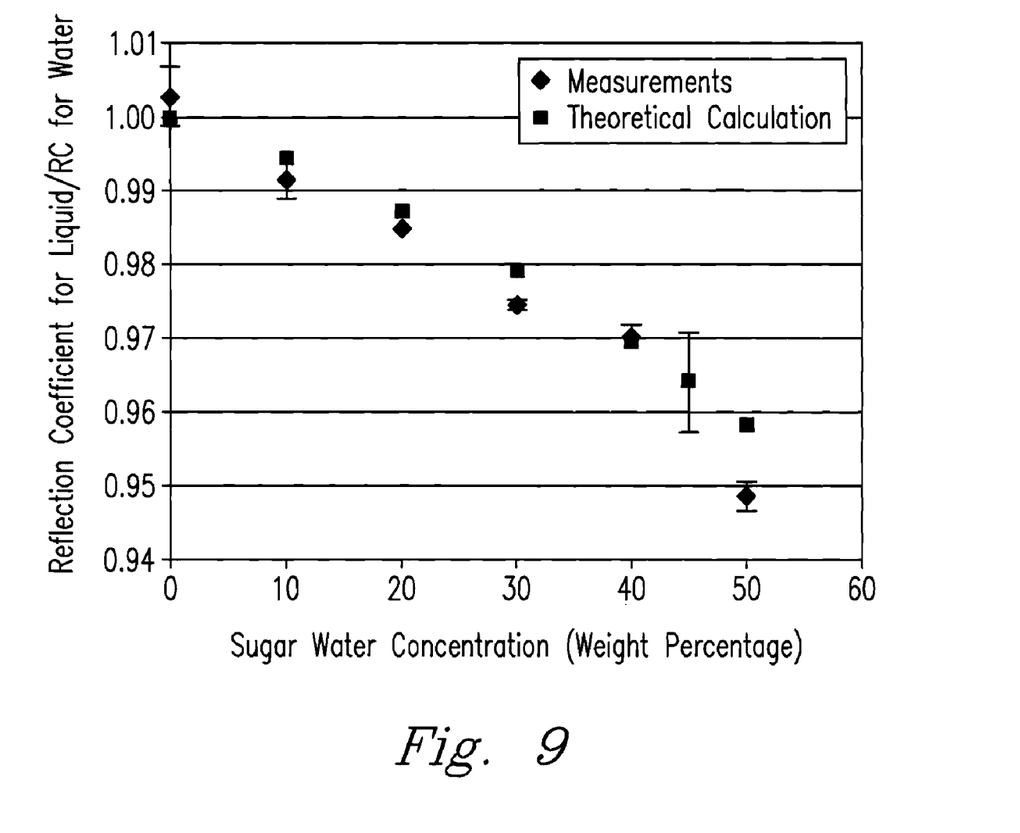
FIG. 9 is a chart showing the correlative results of the measured values for the reflection coefficient compared to the theoretical values.

The theoretical calc lation was carried out using Eq. (19). for water and the six sugar water solutions. in each case, the density of the solution and the velocity of sound in the solution were measured independently by standard techniques. The velocity of sound was obtained by measuring the time-of-flight through the liquid and the density was obtained by weighing a known volume of a sugar water solution. These values were then used in the theoretical formulae in Eq.(14). through Eq. (21). to obtain the reflection coefficient for water and the reflection coefficient for each sugar water solution. For each sugar water solution, the ratio RCliq/RCwtr were obtained and plotted in FIG. 9. The comparison between the experimental and theoretical values in FIG. 9 shows very good agreement.

In a preferred form, the speed of sound in the fluid (c) is determined by performance of multiple reflections of a shear wave at a non-perpendicular, preferably a 45 degree angle of incidence at the solid-liquid interface. Preferably this is performed utilizing a fused quartz window in a pipeline and a 45-degree quartz triangular wedge in contact with the slurry. Because fused quartz has a smaller acoustic impedance (density×velocity of sound) than stainless steel, this design permits very high accuracy in the density measurement because the reflection coefficient for fused quartz is smaller than that for stainless steel, leading to a more sensitive measurement. In addition, more echoes are obtained with quartz because its ultrasonic attenuation is quite small. Calculations indicate that an uncertainty in the density measurement of 0.05% may be possible with the quartz design. In another design the shear wave transducer 31 is directly mounted on the stainless steel pipeline or spool piece and the 45-degree triangular wedge (preferably in a single stainless steel unit) is in contact with the liquid or slurry. In yet another design, the 45-degree wedge consists of two pieces, in which a part of the stainless steel pipeline wall is connected to a 45-degree trapezoid fastened to the wall, such as shown in FIG. 2.

Comparison of the reflection for perpendicular longitudinal waves and the reflection for 45° shear waves show that the sensitivity for the 450 shear waves is 1.5 times that for the perpendicular longitudinal waves. The calculations also show that the 45° angle of incidence is optimum and about 90% of the ultrasound is reflected at the SS-liquid interface. Therefore, even though stainless steel is more attenuative than quartz, a sufficient number of echoes can be observed using a frequency of 2.25 MHz or 1 MHz.

Multiple reflections can be observed for both transducers 30 and 31 and so the self-calibrating feature applies to both transducers. In an alternative embodiment the shear wave inducing transmitter 31 is connected to an angle block 33 that is fastened directly to the wall member 40. While in this embodiment the material for the wedge is the same as the wall, there will undoubtedly be reflections at the interface between the two pieces, but those reflections will not travel to transducer 31. However, due to the multiple reflections and self-calibrating feature, these undesirable reflections will not affect the reflection coefficient measurement at 45°, but the number of echoes may well be reduced and that can affect the accuracy of the density measurement.

However, in either design, the velocity of sound can be determined without passage of ultrasound through a very attenuative medium or through a large vessel.

Preferably, the transducers that are useful for forming and receiving the ultrasound pulse echo series in practicing the present invention can operate in the range of about 0.5 to 20 MHz, more preferably between about 1 and 10 MHz, and most preferably about 5 MHz. However, due to the longer path for incidence at 45°, a smaller frequency such as 1 MHz may be advantageous. In certain applications of the invention, the thickness T of member 40 will be predetermined, and depending on the wavelength of ultrasound in the member 40, the ratio of thickness T to wavelength could be significant, for example greater than about 0.05. As one example, it is contemplated that member 40 would be the existing wall of a stainless steel pipe or container about 0.15 inches thick. For at least some selected ultrasonic frequencies, the wavelength of ultrasound will be significant relative to the wall thickness.

In another form of the invention, because of materials desired for solid member 40 and fluid 25, the acoustic impedance ratio Zsolid/Zliquid will be significant, for example, greater than about [5] five or [10] ten. The multiple reflections serve to amplify the effect of small changes in properties of fluid 25. This amplification occurs because the amplitude of the pulse is diminished in accordance with the reflection coefficient (RCliquid) with each successive reflection with surface 44. Also, because the higher echoes undergo more reflections with surface 44 and because the reflection coefficient (R.Cliquid) is a function of fluid properties, the effect of Thanges in these fluid properties are more pronounced in the higher echo numbers. Consequently, in one form of the invention, it is preferred that at least some of the higher number echoes are used in computing the decay rate.

In further forms of the invention, where reduction of the adverse effects of divergence and/or attenuation is of concern, selection of transducers 30, 31, member 40 dimensions, angle block 33 materials and their associated properties can be of particular interest. For example, the near field can be considered the region immediately in front of an ultrasonic transducer where the sound beam does not diverge and signal loss is at a minimum. The near field length (NO for an ultrasonic transducer can be approximated by Eq. (24)

$$Nf=0.25D^2/\text{lambda} \quad (24)$$

where lambda is the wavelength of the ultrasound in the medium (equal to local speed of sound divided by the frequency) and D is the largest dimension of the transducer face 32 associated with the member 40. For circular transducers, D will be the diameter of the face 32 whereas for rectangular transducers D will be the larger length dimension of the rectangle. In one form of the invention, the near field of the transducer 30 is selected to encompass one or more of the reflections used to calculate the decay rate. In a preferred form a plurality of the echoes used to calculate the decay rate are within the near field length estimated by Eq. (24). in a further preferred form, the majority of the echoes used to calculate the decay rate are within this length.

From an examination of equation (24) one possibility for increasing the near field length is to increase the frequency of the ultrasound. However, there is a practical limit to the effectiveness of this approach, at least because losses due to attenuation of the ultrasound generally increase with increasing frequency. The near field length is therefore preferably maintained at a desired relative length by adjusting the ratio of the size of transducer size D to thickness T. Increasing the transducer size D increases the near field length whereas decreasing T decreases the pathlength of the echoes, allowing more echoes to be detected inside a given near field length, it is to be understood that the pathlength for each echo is the distance the pulse travels for each reflection (2T) times the echo number (the first echo has a pathlength of 2T, the second 4T, the third 6T, etc.). While any ratio can be utilized as would occur to those of skill in the art, in one form of the invention the ratio of D/T is preferably greater than about one. In other forms, the ratio Dif is about two [2] or above.

An advantage is realized by using the decay rate of the echo amplitudes in determining fluid properties. It has been found that, unlike the absolute magnitude of individual echo amplitudes, the slope of echo amplitude versus echo number is substantially independent of characteristics of the ultrasound pulse used to create the echoes. Thus, the self-calibrating feature of the multiple echoes is realized. For example, if the pulser voltage changes by, say, 1%, then each echo changes by the same amount and the Slope of the line, previously described, remains unchanged.

Exemplary materials for solid member 40 and angle block 33 include aluminum, stainless steel, fused quartz, and plastics. Preferably member 40 is non-porous is does not absorb fluid 25. In particular applications, such as food processing and the transport of toxic material, stainless steel or other non-corrosive materials are preferred materials for these pieces.

In a further variation, data transmission between computer 80 and transducers 30, 31 can be achieved wirelessly by provision of appropriate wireless communication devices.

Another application is the design of the unit for placement inside a tank for measurement of the density and velocity of sound. In such a design, the side of the 45° angular wedge could be made watertight so that ultrasound could still reflect from air on one side of the triangle. In another design, a material of known properties could be fastened to the side 45° angular wedge now found in air so that the reflection at this surface can be easily calculated. The reflection at this surface would be less than air, and the reflection at this surface for each echo can be taken into account.

It is also to be understood that another embodiment of the present invention is a unique technique to determine fluid properties wherein an ultrasonic transducer 30 is provided on a surface 42 of a solid member 40 having an opposed second surface 44 in contact with the fluid 25. A second ultrasonic transducer 31 configured to transmit a shear wave to the interface 23 between the fluid 25 and the material is also provided. This technique can include delivering an ultrasonic pulse through these two transducers 30, 31 detecting a multiplicity of pulse echoes caused by reflections of the ultrasonic pulse between the solid-fluid interface and the transducer-solid interface, and determining the decay rate of the detected echo amplitude as a function of echo number. The determined decay rate is compared to a calibrated decay rate, such as obtained using water or another calibration fluid, to determine an acoustic property of the fluid. In some applications this includes a reflection coefficient which can be further calculated to obtain a value such as the density of the material or the velocity of sound through the fluid.

While the invention has been illustrated and described in detail in the drawings and foregoing description, the same is to be considered illustrative and not restrictive in character, it being understood that only the preferred embodiment has been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least one", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A method for determining a fluid property comprising the steps of:
    delivering a first ultrasound pulse to a member with a transducer, the member being comprised of a solid material and including a first surface opposite a second surface, the first surface being coupled to the transducer and the second surface being in contact with a fluid, the ultrasound pulse reflecting between the first surface and the second surface to provide a first ultrasound pulse echo series;
    detecting a multiplicity of the ultrasound pulse echoes of the echo series with the transducer;
    delivering a second ultrasound pulse through a shear wave transducer, the shear wave transducer configured to provide a pulse at a general angle of 45 degrees relative to the interface of said second surface and said fluid to obtain a second ultrasound pulse echo series;
    detecting a multiplicity of ultrasound pulse echoes of said second ultrasound pulse echo sound series with said shear wave transducer;
    determining a first value from the multiplicity of pulse echoes of the first ultrasound pulse echo series;
    determining a second value from the multiplicity of pulse echoes of the second ultrasound pulse echo series; and
    determining a physical property of the fluid utilizing said first and second values.

2. The method of claim 1 wherein said physical property is selected from the group consisting essentially of velocity, density and combinations thereof.

3. The method of claim 1 wherein said step of determining a physical property comprises comparing measurements of reflection coefficients with a theoretical calculation to extract the density of the material and the velocity of sound in the material.

4. The method of claim 3 wherein the reflection coefficients are obtained by plotting the natural log of the ratio of FFT amplitudes against an echo number and finding the slope of this line.

5. The method of claim 1 wherein the transducer produces the ultrasonic pulse in response to a voltage input from a pulser and wherein the first value is determined by selecting a peak echo amplitude at a predetermined frequency for each of the detected echoes and determining a value corresponding to an average decay rate of the selected peak echo amplitude for each of the multiplicity of ultrasound pulse echoes as a function of echo number.

6. The method of claim 5 wherein the transducer produces an output signal in response to the detecting and the transducer output signal is digitized and transformed from time domain to frequency domain prior to selection of the peak echo amplitude for each of the multiplicity of ultrasound pulse echoes.

7. The method of claim 5 wherein at least two of the multiplicity of ultrasound pulse echoes are detected during the detecting steps.

8. The method of claim 1 wherein the first ultrasonic pulse is a longitudinal wave and the physical property is fluid density.

9. The method of claim 1 wherein the second ultrasonic pulse is a shear wave and the physical property is selected from the group consisting of the velocity of sound, the density of the liquid and combinations thereof.

10. A system for determining a fluid property comprising:
    a longitudinal ultrasonic transducer, operably connected to an interface between a solid and a fluid, said longitudinal ultrasonic transducer configured to send and receive ultrasonic transmissions;
    a shear wave transducer operably connected at a general angle of 45 degrees to an interface between said solid and said fluid, said shear wave transducer operably configured to send and receive ultrasonic transmissions; and
    a computing device configured to receive information from said longitudinal ultrasonic transducer and said shear wave transducer and to perform a preselected program of method steps to determine a preselected value correlating to said fluid property.

11. The system of claim 10 wherein said shear wave transducer is operatively connected at a preselected angle to an angle block made of fused quartz whereby said shear wave transducer transmits an ultrasonic wave at a generally 45 degree angle.

12. A method for determining a fluid property comprising the steps of:
    delivering an ultrasound pulse to a member with a transducer, the member being comprised of a solid material and including a first surface opposite a second surface, the first surface being coupled to the transducer and the second surface being in contact with a fluid, the ultrasound pulse reflecting between the first surface and the second surface to provide a first ultrasound pulse echo series;

detecting a multiplicity of the ultrasound pulse echoes of the echo series with the transducer;

delivering an ultrasound pulse through a shear wave transducer, the shear wave transducer configured to provide a pulse at a predefined angle relative to the interface of said second surface and said fluid to obtain a second ultrasound pulse echo series;

detecting a multiplicity of ultrasound pulse echo of said second ultrasound pulse echo sound series with said shear wave transducer;

determining a first value from the multiplicity of pulse echoes of the first ultrasound pulse echo series;

determining a second value from the multiplicity of pulse echoes of the second ultrasound pulse echo series; and determining the velocity of sound and density of the fluid utilizing said first and second values.

* * * * *

UNITED STATES PATENT AND TRADEMARK OFFICE
CERTIFICATE OF CORRECTION

PATENT NO. : 7,966,882 B2
APPLICATION NO. : 12/108161
DATED : June 28, 2011
INVENTOR(S) : Margaret Stautberg Greenwood It is certified that error appears in the above-identified patent and that said Letters Patent is hereby corrected as shown below:

Column 3, line 7 and 8: replace "tansducer30" with "transducer 30"
Column 3, line 11: replace "echo. in" with "echo. In"
Column 3, line 14: insert --into-- before "member 40"
Column 4, line 65: replace "EFT" with "FFT"
Column 5, line 26: replace "EFT" with "FFT"
Column 6, line 3: replace "(Zliquidlis" with "(Zliquid), is"
Column 7, line 14: replace "syn bol" with "symbol"
Column 7, line 67: replace "(ST)" with "(SV)"
Column 8, line 2: replace "can e" with "can be"
Column 8, line 23: replace "PFT" with "FFT"
Column 8, line 25: replace "HT" with "FFT"
Column 8, line 41: replace "in Fig. Fig. 9" with "in Fig. 9"
Column 8, line 43: replace "RCwir" with "RCwtr"
Column 8, line 44: replace "calc lation" with "calculation"
Column 9, line 63: replace "(R.Cliquid)" with "(RCliquid)"
Column 9, line 64: replace "Thanges" with "changes"
Column 10, line 8: replace "(NO)" with "(Nf)"
Column 10, line 42: replace "Dif" with "D/T"

Signed and Sealed this
Thirteenth Day of March, 2012

David J. Kappos
*Director of the United States Patent and Trademark Office*